(12) United States Patent
Feurer et al.

(10) Patent No.: US 7,410,973 B2
(45) Date of Patent: Aug. 12, 2008

(54) 4-AMINO-SUBSTITUTED PYRIMIDINE DERIVATIVES

(75) Inventors: Achim Feurer, Wilhelmsfeld (DE); Joachim Luithle, Wülfrath (DE); Stephan-Nicholas Wirtz, Wuppertal (DE); Gerhard König, Arlington, MA (US); Johannes-Peter Stasch, Solingen (DE); Elke Stahl, Bergisch Gladbach (DE); Rudy Schreiber, Menlo Park, CA (US); Frank Wunder, Wuppertal (DE); Dieter Lang, Velbert (DE)

(73) Assignee: Bayer Healthcare AG, Leverkusen (DE)

( * ) Notice: Subject to any disclaimer, the term of this patent is extended or adjusted under 35 U.S.C. 154(b) by 265 days.

(21) Appl. No.: 10/521,540

(22) PCT Filed: Jul. 7, 2003

(86) PCT No.: PCT/EP03/07236

§ 371 (c)(1), (2), (4) Date: Jul. 11, 2005

(87) PCT Pub. No.: WO2004/009590

PCT Pub. Date: Jan. 29, 2004

(65) Prior Publication Data

US 2006/0014951 A1    Jan. 19, 2006

(30) Foreign Application Priority Data

Jul. 18, 2002    (DE) ............................... 102 32 571

(51) Int. Cl.
*C07D 471/04* (2006.01)
*A61K 31/505* (2006.01)

(52) U.S. Cl. ..................... 514/256; 544/328
(58) Field of Classification Search ................. 544/328; 514/256

See application file for complete search history.

(56) References Cited

FOREIGN PATENT DOCUMENTS

| DE | 19834045 | 2/2000 |
|---|---|---|
| DE | 19846514 | 4/2000 |
| WO | 0242301 | 5/2002 |

OTHER PUBLICATIONS

Vippagunta et al., Crystalline Solids, Advanced Drug Delivery Reviews 48:3-26, 2001.*
West, Solid Solutions, Solid State Chemistry and Its Applications, pp. 365, 1988.*
Carvajal et al., Molecular Mechanism of cGMP-mediated Smooth Muscle Relaxation, Journal of Cellular Physiology, 184:409-420, 2000.*
Yamashita et al., Mechanisms of Reduced Nitric Oxide/cGMP-mediated Vasorelaxation in Transgenic Mice Overexpressing Endothelial Nitric Oxide Synthase, Hypertension, 36:97-102, 2000.*
Fisker et al., PubMed Abstract (J Endocrinol Invest. 22(5 Suppl):89-93) 1999.*
Layzer, Degenerative Diseases of the Nervous System, Cecil Textbook of Medicine, 20th Edition, vol. 2, pp. 2050-2057, 1996.*
Damasio, Alzheimer's Disease and the related dementias, Cecil Textbook of Medicine, 20th Edition, vol. 2, pp. 1992-1996, 1996.*
Straub, et al., "NO-Independent Stimulators of Soluble Guanylate Cyclase," *Bioorganic & Medicinal Chemistry Letters*, 11 (6): 781-784 (2001).

* cited by examiner

*Primary Examiner*—Deepak Rao
(74) *Attorney, Agent, or Firm*—Edwards Angell Palmer & Dodge LLP; Barry Kramer; Ralph A. Loren

(57) ABSTRACT

The present invention relates to novel 4-amino-substituted pyrimidine derivatives which stimulate soluble guanylate cyclase, to processes for the preparation thereof, and to the use thereof for producing medicaments, in particular medicaments for the treatment of central nervous system diseases.

7 Claims, No Drawings

4-AMINO-SUBSTITUTED PYRIMIDINE DERIVATIVES

The present invention relates to novel 4-amino-substituted pyrimidine derivatives which stimulate soluble guanylate cyclase, to process for the preparation thereof, and to the use thereof for producing medicaments, in particular medicaments for the treatment of central nervous system diseases.

One of the most important cellular signal transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and contain at least one heme per heterodimer. The heme groups are part of the regulatory center and are of central importance for the mechanism of activation. NO is able to bind to the iron atom of heme and thus markedly increase the activity of the enzyme. Heme-free preparations cannot, by contrast, be stimulated by NO. CO is also able to bind to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed. In Alzheimers patients for example the NO-stimulated activity of soluble guanylate cyclase in the brain (cerebral cortex) is greatly reduced.

A reduced learning behavior can be observed in experimental animals on administration of dizocilpine, which leads to a reduced cGMP level (Yamada et al., Neuroscience 74 (1996), 365-374). This impairment can be abolished by injecting 8-Br-cGMP, a membrane-permeable form of cGMP. This is consistent with investigations showing that the cGMP level in the brain is increased after learning and memory tasks.

A possible treatment which is independent of NO and aims at influencing the cGMP signal pathway in organisms is a promising approach for stimulating soluble guanylate cyclase because of the high efficiency and few side effects which are to be expected.

Compounds, such as organic nitrates, whose effect is based on release of NO have to date been exclusively used for the therapeutic stimulation of soluble guanylate cyclase. NO is produced by bioconversion and activates soluble guanylate cyclase by binding to the central iron atom of heme. Besides the side effects, the development of tolerance is one of the crucial disadvantages of this mode of treatment.

Substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al., J. Biol. Chem. 252 (1977), 1279), diphenyliodonium hexafluorophosphate (Petibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569, WO 00/21954, WO 02/4229, WO 02/4300, WO 02/4301 and WO 02/4302 describe pyrazolopyridine derivatives as stimulators of soluble guanylate cyclase. Also described in these patent applications are pyrazolopyridines having various radicals. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation and their metabolic pathway.

It was therefore the object of the present invention to provide further pyrimidine derivatives which act as stimulators of soluble guanylate cyclase but do not have the disadvantages, detailed above, of the compounds from the prior art. An additional advantage of novel medicaments for the treatment of central nervous system diseases (e.g. learning and memory impairments) would be an increased selectivity for peripheral cardiovascular effects. It was likewise intended to improve these (e.g. by better brain penetration) compared with the prior art.

This object is achieved according to the present invention by the compounds claimed in claim 1.

Specifically, the present invention relates to the compounds of the formula

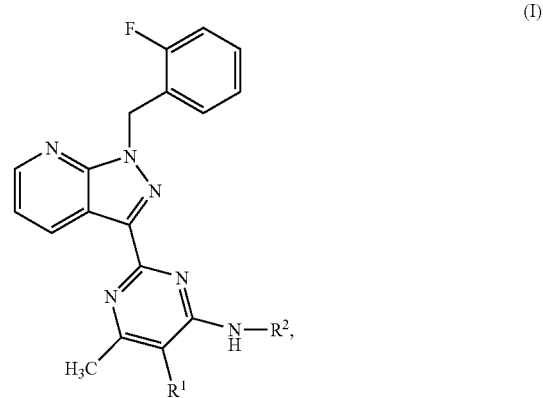

(I)

in which
R$^1$ is hydrogen or fluorine,
R$^2$ is C$_1$-C$_6$-alkyl which may be substituted by C$_1$-C$_4$-alkoxy, C$_3$-C$_6$-cycloalkyl, C$_6$-C$_{10}$-aryl, 5- to 6-membered heteroaryl, where C$_6$-C$_{10}$-aryl and 5- to 6-membered heteroaryl are optionally substituted by up to 3 radicals selected from the group of halogen, C$_1$-C$_4$-alkyl, C$_1$-C$_4$-alkoxyl, trifluoromethoxy, and the salts, solvates and/or solvates of the salts thereof.

Where asymmetric C atoms are present in R$^2$, the compounds of the invention can be in the form of enantiomers, diastereomers or mixtures thereof. These mixtures can be separated in a known manner into the stereoisomerically pure constituents.

Salts preferred for the purposes of the invention are physiologically acceptable salts of the compounds of the invention.

Physiologically acceptable salts of the compounds according to the invention may be acidic addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may also be salts with usual bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or methylpiperidine.

Solvates of the compounds of the invention are for the purposes of the invention stoichiometric compositions of the compounds or of their salts with solvents, e.g. water, ethanol.

For the purposes of the present invention, the substituents generally have the following meaning:

$C_1$-$C_6$-alkyl is a straight-chain or branched alkyl radical having 1 to 6 carbon atoms. Preference is given to a straight-chain or branched alkyl radical having 1 to 4, particularly preferably having 1 to 3, carbon atoms. Nonlimiting examples include methyl, ethyl, n-propyl, isopropyl, tert-butyl, n-pentyl and n-hexyl.

$C_1$-$C_6$-alkoxy is a straight-chain or branched alkoxy radical having 1 to 6 carbon atoms. Preference is given to a straight-chain or branched alkoxy radical having 1 to 4, particularly preferably having 1 to 3, carbon atoms. Nonlimiting examples include methoxy, ethoxy, n-propoxy, isopropoxy, tert-butoxy, n-pentoxy and n-hexoxy.

$C_6$-$C_{10}$-aryl is an aromatic radical having 6 to 10 carbon atoms. Nonlimiting examples include phenyl and naphthyl.

$C_3$-$C_8$-cycloalkyl is cyclopropyl, cyclopentyl, cyclobutyl, cyclohexyl, cycloheptyl or cyclooctyl. Nonlimiting examples include cyclopropyl, cyclopentyl and cyclohexyl.

Halogen is fluorine, chlorine, bromine and iodine. Fluorine, chlorine and bromine are preferred. Fluorine and chlorine are particularly preferred.

5- to 6-membered heteroaryl is an aromatic, monocyclic radical having 5 to 6 ring atoms and up to 3 heteroatoms from the series S, O and/or N. 5-membered heteroaryls having one heteroatom are preferred. The heteroaryl radical may be bonded via a carbon or nitrogen. Nonlimiting examples include thienyl, furyl, pyrrolyl, thiazolyl, oxazolyl, imidazolyl, pyridyl, pyrimidyl, pyridazinyl, isoxazyl.

Where the radicals in the compounds of the invention are substituted, the radicals may, unless otherwise specified, have one or more identical or different substituents. Substitution by up to three identical or different substituents is preferred. Substitution by one substituent is very particularly preferred.

Combinations of two or more of the preferred ranges mentioned above are very particularly preferred.

A further embodiment of the invention relates to compounds of the formula (I) in which $R^1$ is hydrogen or fluorine, $R^2$ is $C_1$-$C_5$-alkyl which may be substituted by methoxy, ethoxy, isopropoxy, cyclopropyl, or benzyl, phenethyl, which are optionally substituted by up to 3 radicals selected from the group of fluorine, methyl, methoxy, trifluoromethoxy, or thienyl, and the salts, solvates and/or solvates of the salts thereof.

The invention further relates to a process for preparing the compounds of the invention, in which compounds of the formula

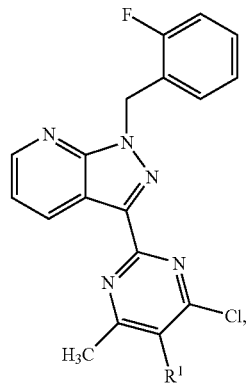

(II)

in which $R^1$ has the meanings indicated above, are reacted with a compound of the formula

$H_2N—R^2$ (III), in which $R^2$ has the meanings indicated above, in an inert solvent, and the resulting compounds of the formula (I) are reacted where appropriate with the appropriate (i) solvents and/or (ii) bases or acids to give the solvates, salts and/or solvates of the salts thereof.

The process of the invention is preferably carried out in a temperature range from 40 to 100° C. under atmospheric pressure.

Examples of inert solvents are ethers such as dioxane, tetrahydrofuran or 1,2-dimethoxyethane, hydrocarbons such as benzene, xylene or toluene, nitroaromatics such as nitrobenzene, optionally N-alkylated carboxamides such as dimethylformamide, dimethylacetamide, alkyl sulfoxides such as dimethyl sulfoxide or lactams such as N-methylpyrrolidone. Solvents from the series of dimethylformamide and dimethyl sulfoxide are preferred.

Compounds of the formula (II) can be prepared by the process disclosed in WO 00/06569 starting from compounds of the formula

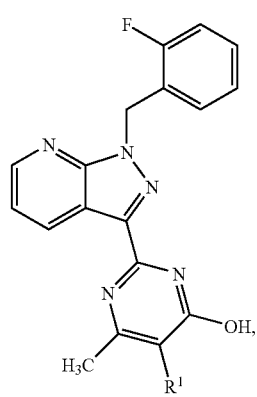

(IV)

in which $R^1$ has the meanings indicated above.

Compounds of the formula (IV) can be prepared by reacting compounds of the formula

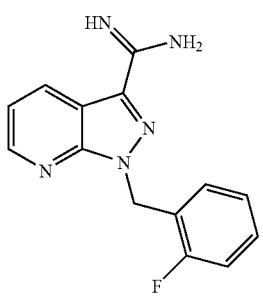

with compounds of the formula

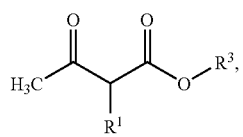

Synthesis scheme:

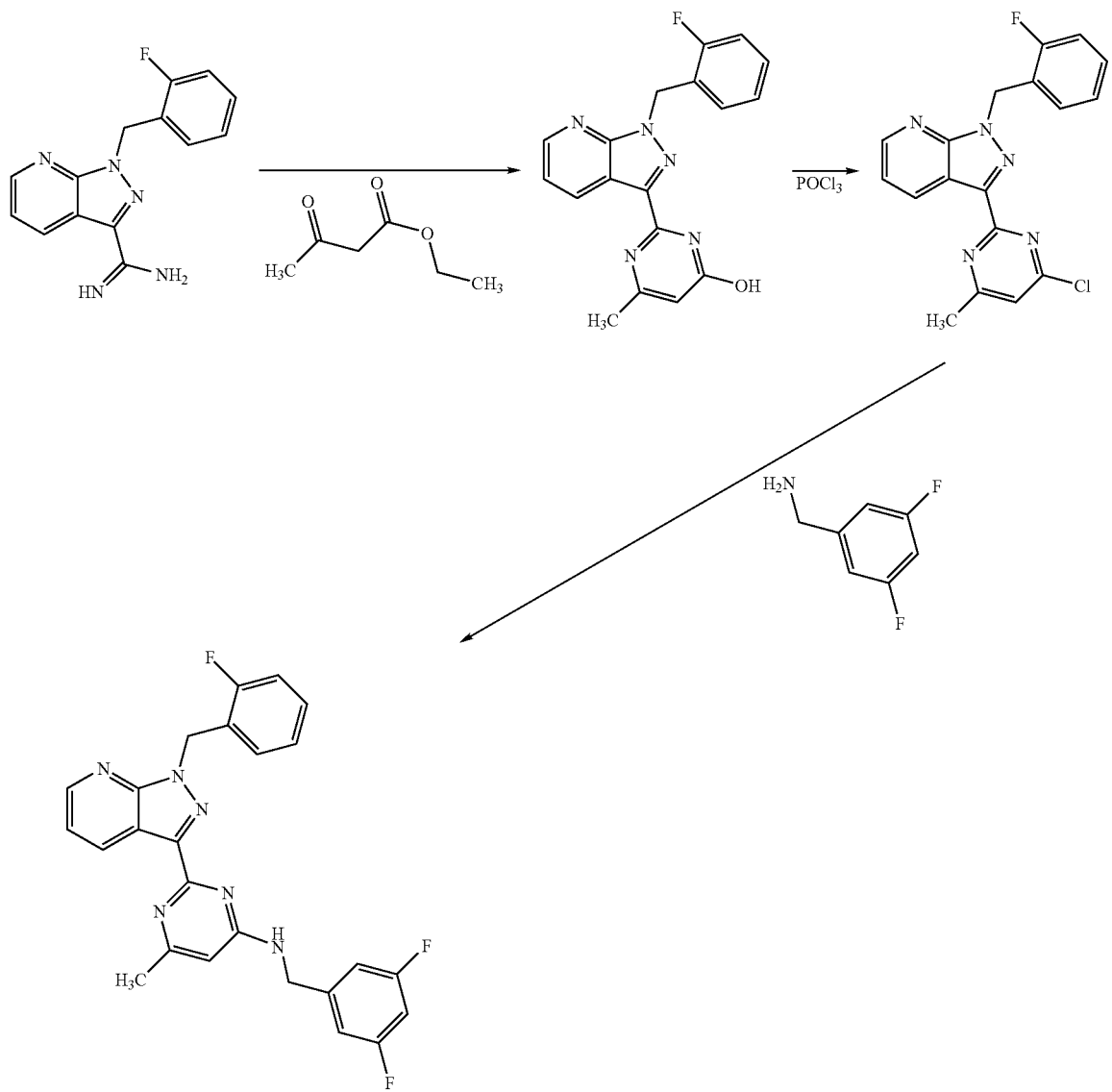

(V)

in which

R[1] has the meanings indicated above, and

R[3] is straight-chain $C_1$-$C_6$-alkyl, in an inert solvent.

The process of the invention is preferably carried out in a temperature range from 50 to 150° C. under atmospheric pressure.

The compounds of the formula (VI) are commercially available, known or can be prepared by known processes.

The compound of the formula (V) is disclosed in WO 00/06569.

The process of the invention can be illustrated by the following synthesis scheme.

The compounds of the invention show a valuable range of pharmacological effects which could not have been predicted.

The compounds of the invention increase the cGMP levels in neurons and thus represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, cranicerebral trauma, stroke, dementia occurring after strokes (post stroke dementia), post-traumatic cranial cerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis.

The compounds of the invention also lead to vasorelaxation, platelet aggregation inhibition and to a reduction in blood pressure, and to an increase in the coronary blood flow. These effects are mediated by direct stimulation of soluble guanylate cyclase and an intracellular cGMP increase. In addition, the compounds of the invention may enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies by use in stents for example, percutaneously transluminal angioplasties (PTAs), percutaneously transluminal coronary angioplasties (PTCAs), bypass operations and for the treatment of arteriosclerosis, asthmatic disorders, osteoporosis, gastroparesis, glaucoma and diseases of the urogenital system such as, for example, incontenence, prostate hypertrophy, erectile dysfunction and female sexual dysfunction.

They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds of the invention are additionally suitable for controlling cerebral blood flow and may represent effective agents for controlling migrain.

They are also suitable for the prophylaxis and control of the sequelae of cerebral infarctions such as stroke, cerebral ischemias and craniocerebral trauma. The compounds of the invention can likewise be employed for controlling states of pain.

In addition, the compounds of the invention have an anti-inflammatory effect.

Furthermore, the invention encompasses the combination of the compounds of the invention with organic nitrates and NO donors.

Organic nitrates and NO donors for the purposes of the invention are generally substances which release NO or NO species. Preference is given to sodium nitroprusside, nitroglycerine, isosorbide dinitrate, isosorbide mononitrate, molsidomine and SIN-1.

In addition, the invention encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TIPS 11 pp. 150 to 155. These inhibitors potentiate the effect of the compounds of the invention, and the desired pharmacological effect is increased.

The in vitro effect of the compounds of the invention can be shown in the following assays:

Increase of cGMP in Primary Cortical Neurons

Rat embryos (embryonic day 17-19) are decapitated, and the cerebrum is removed and incubated with 5 ml of papain solution and 250 µl of DNAse (papain kit from Cell-System) at 37° C. for 30 min, homogenized using a Pasteur pipette and centrifuged at 1200 rpm for 5 min. The supernatant is removed, the cell pellets resuspended (in 2.7 ml of EBSS [Earl's balanced salt solution], 300 µl of ovomucoid/albumin (conc.) solution, 150 µl of DNAse; papain kit from Cell-System), layered over 5 ml of ovomucoid/albumin solution and centrifuged at 700 rpm for 6 min. The supernatant is removed, the cells are resuspended in cultivation medium (Gibco neurobasal medium, B27 Supplement 50×1 ml/100 ml, 2 mM L-glutamine), counted (approx. 150 000 cells/well) and plated out on Poly-D-lysine-coated 96-well plates (Costar) with 200 µl/well. After 6-7 days at 37° C. (5% $CO_2$), the neurons are freed of culture medium and washed once with assay buffer (154 mM NaCl, 5.6 mM KCl, 2.3 mM $CaCl_2 2H_2O$, 1 mM $MgCl_2$, 5.6 mM glucose, 8.6 mM HEPES (4-(2-hydroxyethyl)piperazine-1-ethanesulfonic acid), pH=7.4). 100 µl/well test substance are dissolved in assay buffer and then 100 µl/well IBMX (3-isobutyl-1-methylxanthine; dissolved in 50 mM ethanol, diluted with assay buffer to a final concentration of 100 µM) are added. After incubation at 37° C. for 20 min, the assay buffer is replaced by 200 µl/well of lysis buffer (cGMP EIA RPN 226 from Amersham Pharmacia Biotech), and the cGMP content of the lysates is determined using an EIA assay kit.

Vasorelaxant Effect In Vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated (dissolved in 5 µl DMSO) is investigated in each further run in increasing dosage in each case, and the height of the contraction is compared with the height of the contraction reached in the last preceding control cycle(=control value). The concentration necessary to reduce the height of the control value by 50% ($IC_{50}$) is calculated from this.

Determination of the Liver Clearance In Vitro

Rats are anesthetized, heparinized, and the liver is perfused in situ via the portal vein. Primary rat hepatocytes are then obtained ex vivo from the liver using collagenase solution. $2.10^6$ hepatocytes per ml were incubated at 37° C. with the same concentration in each case of the compound to be investigated. The decrease of the substrate to be investigated over time was determined bioanalytically (HPLC/UV, HPLC/fluorescence or LC/MSMS) at 5 points in time in each case in the period from 0-15 min after the start of incubation. From this, the clearance was calculated by means of the cell count and liver weight.

Determination of the Plasma Clearance In Vivo

The substance to be investigated is administered as a solution intravenously to rats via the tail vein. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The suitability of the compounds of the invention for the treatment of disorders of perception, concentration, learning and/or memory can be shown for example in the following animal model:

Determination of the Learning and Memory In the Social Recognition Test

Adult Wistar rats (Winkelmann, Borchen; 4-5 months) and 4-5-week old pups are accustomed to their new environment for one week, with 3 animals being housed in each cage (Makrolon type IV) in a 12 h day-night rhythm (light on at 06:00) with water and food ad libitum. Usually, 4 groups of 10 animals (1 vehicle control group, 3 substance-treated groups) are tested. Firstly, all animals undergo a habituation run as in trial 1 but without substance or vehicle administration. The test substances are administered directly after trial 1. The social memory is measured in trial 2 after 24 h.

Trial 1: 30 min before testing, the adult rats are housed singly in cages (Makrolon type IV). 4 min before testing, a box consisting of two aluminum side walls, an aluminum back wall and a Plexiglas front (63×41×40 cm) is fitted over the cage, and the lid of the cage is removed. A pup is put with the adult rats in the cage, and the social interaction (e.g. sniffing) is timed for 2 min with a stopclock. The animals are then returned to their cage.

Trial 2: The test is repeated with the same animals after 24 h in analogy to trial 1. The difference between the social interaction time in trial 1 and trial 2 is taken as a measure of the social memory.

The compounds of the invention are suitable for use as medicaments for humans and animals.

The present invention includes pharmaceutical preparations which, besides inert, nontoxic, pharmaceutically suitable excipients and carriers, comprise one or more compounds of the invention, or which consist of one or more compounds of the invention, and processes for producing these preparations.

The compounds of the invention are to be present in these preparations in a concentration of from 0.1 to 99.5% by weight, preferably from 0.5 to 95% by weight, of the complete mixture.

The pharmaceutical preparations may, apart from the compounds of the invention, also comprise other active pharmaceutical ingredients.

The pharmaceutical preparations mentioned above can be produced in a conventional way by known methods, for example with the excipient(s) or carrier(s).

The novel active ingredients can be converted in a known manner into the usual formulations such as tablets, coated tablets, pills, granules, aerosols, syrups, emulsions, suspensions and solutions, using inert, nontoxic, pharmaceutically suitable carriers or solvents. In these cases, the therapeutically effective compound is to be present in each case in a concentration of about 0.5 to 90% by weight of the complete mixture, i.e. in amounts which are sufficient to achieve the indicated dosage range.

The formulations can be produced for example by diluting the active ingredients with solvents and/or carriers, where appropriate using emulsifiers and/or dispersants, it being possible for example in the case where water is used as diluent where appropriate to use organic solvents as auxiliary solvents.

Administration can take place in a conventional way, preferably orally, transdermally or parenterally, in particular perlingually or intravenously. However, it can also take place by inhalation through the mouth or nose, for example with the aid of a spray, or topically via the skin.

It has generally proved to be advantageous to administer amounts of about 0.001 to 10 mg/kg, on oral administration preferably about 0.005 to 3 mg/kg, of body weight to achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, where in other cases the stated upper limit must be exceeded. If larger amounts are administered, it may be advisable to divide these into a plurality of single doses over the day.

Abbreviations:

| | |
|---|---|
| ACN | acetonitrile |
| DAD | diode array detector |
| DCM | dichloromethane |
| DME | 1,2-dimethoxyethane |
| DMF | N,N-dimethylformamide |
| DMSO | dimethyl sulfoxide |
| ESI | electrospray ionization (in MS) |
| HPLC | high pressure, high performance liquid chromatography |
| LC-MS | coupled liquid chromatography-mass spectroscopy |
| m.p. | melting point |
| MS | mass spectroscopy |
| NMR | nuclear magnetic resonance spectroscopy |
| $R_f$ | retention index (in TLC) |
| RT | room temperature |
| $R_t$ | retention time (in HPLC) |
| TFA | trifluoroacetic acid |
| THF | tetrahydrofuran |

Analytical Methods:

HPLC

Instrument: HP 1100 with DAD detection; column: Kromasil RP-18, 60 mm×2 mm, 3.5 µm; eluent: A=5 ml perchloric acid/l $H_2O$, B=ACN; gradient: 0 min 2% B, 0.5 min 2% B, 4.5 min 90% B, 6.5 min 90% B; flow rate: 0.75 ml/min; temp.: 30° C.; UV detection: 210 nm.

Preparative HPLC

Column: YMC GEL ODS-AQS-11 µm, 250 mm×30 mm; eluent: A=$H_2O$, B=ACN; gradient: 0 min 10% B, 10 min 10% B, 35 min 100% B, 45 min 100% B; flow rate: 33 ml/min; temp.: about 22° C.; UV detection: 254 nm.

LC/MS

Method A:

Instrument: Finnigan MAT 900S, TSP: P4000, AS3000, UV3000HR; column: Symmetry C 18, 150 mm×2.1 mm, 5.0 µm; eluent C: water, eluent B: water+0.3 g of 35% hydrochloric acid, eluent A: ACN; gradient: 0 min 2% A→2.5 min 95% A→5 min 95% A; oven: 70° C.; flow rate: 1.2 ml/min; UV detection: 210 nm.

Method B:

Instrument: Finnigan MAT 900S, TSP: P4000, AS3000, UV3000HR; column: Symmetry C 18, 150 mm×2.1 mm, 5.0 µm; eluent A: acetonitrile, eluent B: water+0.6 g of 30% hydrochloric acid; gradient: 0 min 10% A→4 min 90% A→9 min 90% A; oven: 50° C.; flow rate: 0.6 ml/min; UV detection: 210 nm.

Method C:

Instrument: Micromass Quattro LCZ, HP 1100; column: Symmetry C 18, 50 mm×2.1 mm, 3.5 µm; eluent A: acetonitrile+0.1% formic acid, eluent B: water+0.1% formic acid; gradient: 0 min 10% A→4 min 90% A→6 min 90% A; oven: 40° C.; flow rate: 0.5 ml/min; UV detection: 208-400 nm.

Method D:

Instrument: Micromass Platform LCZ, HP1100; column: Symmetry C 18, 50 mm×2.1 mm, 3.5 µm; eluent A: acetonitrile+0.1% formic acid, eluent B: water+0.1% formic acid; gradient: 0 min 10% A→4 min 90% A→6 min 90% A; oven: 40° C.; flow rate: 0.5 ml/min; UV detection: 208-400 nm.

Starting Compounds:

EXAMPLE I

Step 1

Ethyl 5-amino-1-(2-fluorobenzyl)pyrazole-3-carboxylate

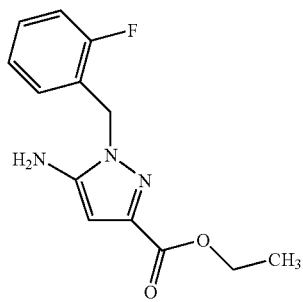

111.75 g (75 ml, 0.98 mol) of trifluoroacetic acid are added to 100.00 g (0.613 mol) of the sodium salt of ethyl cyanopyruvate (prepared in analogy to Borsche and Manteuffel, Liebigs Ann. 1934, 512, 97) while stirring efficiently in 2.5 l of dioxane at room temperature under argon, and the mixture is stirred for 10 min, during which most of the precursor dissolves. Then 85.93 g (0.613 mol) of 2-fluorobenzyl-hydrazine are added, and the mixture is boiled overnight. After cooling, the precipitated sodium trifluoroacetate crystals are filtered off with suction and washed with dioxane, and the crude solution is reacted further.

Step 2

Ethyl 1-(2-fluorobenzyl)-1H-pyrazolo[3,4-b]pyridine-3-carboxylate

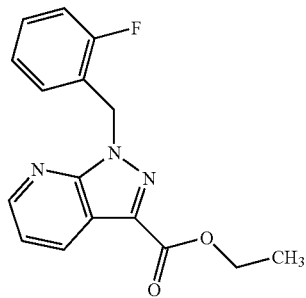

The solution obtained in step 1 is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is poured into 2 l of water and extracted three times with 1 l of ethyl acetate each time. The combined organic phases are dried with magnesium sulfate and concentrated in vacuo. Chromatography is carried out on 2.5 kg of silica gel, eluting with a toluene/toluene-ethyl acetate=4:1 gradient.

Yield: 91.6 g (49.9% of theory over two stages).

M.p.: 85° C.

$R_f$(silica gel, toluene/ethyl acetate 1:1): 0.83

Step 3

1-(2-Fluorobenzyl)-1H-pyrazolo[3,4-b]pyridine-3-carboxamide

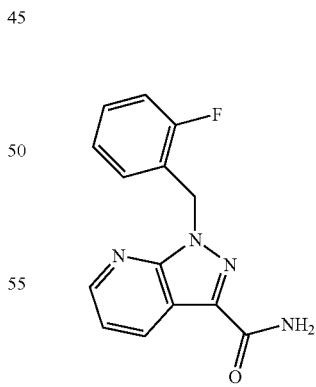

10.18 g (34 mmol) of the ester obtained in step 2 are introduced into 150 ml of methanol saturated with ammonia at 0-10° C. Stirring at room temperature for two days is followed by concentration in vacuo.

$R_f$(silica gel, toluene/ethyl acetate 1:1): 0.33

Step 4

3-Cyano-1-(2-fluorobenzyl)-1H-pyrazolo[3,4-b]pyridine

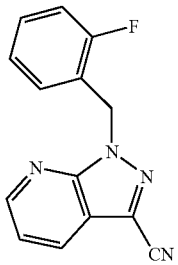

36.10 g (133 mmol) of 1-(2-fluorobenzyl)-1H-pyrazolo[3,4-b]pyridine-3-carboxamide from step 3 are dissolved in 330 ml of THF, and 27.00 g (341 mmol) of pyridine are added. Then, over the course of 10 min, 47.76 ml (71.66 g, 341 mmol) of trifluoroacetic anhydride are added, during which the temperature rises to 40° C. The mixture is stirred at room temperature overnight. The mixture is then poured into 1 l of water and extracted three times with 0.5 l of ethyl acetate each time. The organic phase is washed with saturated sodium bicarbonate solution and with 1 N, dried with and concentrated in vacuo.

Yield: 33.7 g (100% of theory)
M.p.: 81° C.
$R_f$(silica gel, toluene/ethyl acetate 1:1): 0.74

Step 5

1-(2-Fluorobenzyl)-1H-pyrazolo[3,4-b]pyridine-3-carboximidamide

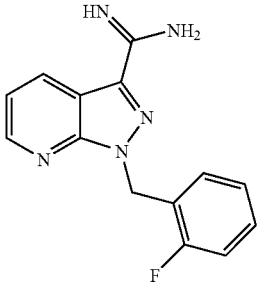

108.00 g (0.43 mol) of 1-(2-fluorobenzyl)-1H-pyrazolo[3,4-b]pyridine-3-carbonitrile (example I, step 4) are dissolved in one liter of methanol and added dropwise to a solution of 94.73 g (1.67 mol; purity: 95%) of sodium methoxide in 3 l of methanol.

After stirring at RT for 2 hours, 28.83 g (0.54 mol) of solid ammonium chloride are added, and subsequently 100.03 g (1.67 mol) of glacial acetic acid are added dropwise. This solution is stirred under reflux overnight. The solvent is removed in vacuo, the residue is twice suspended in acetone and the insoluble solid is filtered off with suction. The latter is dissolved in 1.5 l of ethyl acetate, and 590 ml of an aqueous 20% strength sodium carbonate solution are added. Stirring for 20 minutes is followed by dilution with 200 ml of 1N sodium hydroxide solution. The organic phase is washed with saturated aqueous sodium chloride solution, dried over magnesium sulfate and filtered. The solvent is removed in vacuo. 99.10 g (86% of theory) of the product are obtained.

LC/MS (method B): $R_t$=2.25 min.
MS (ESIpos): m/z=270 (M+H)+
$^1$H-NMR (300 MHz, DMSO-$d_6$): δ=5.79 (s, 2H), 6.54 (br s, 3H), 7.09-7.18 (m, 2H), 7.23 (t, 1H), 7.31-7.41 (m, 2H), 8.62 (d, 1H), 8.69 (d, 1H).

Step 6

2-[1-(2-Fluorobenzyl)-1H-pyrazolo[3,4-b]pyridin-3-yl]-6-methyl-4-pyrimidinol

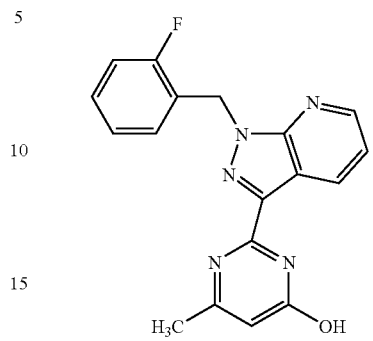

2.00 g (7.43 mmol) of 1-(2-fluorobenzyl)-1H-pyrazolo[3,4-b]pyridine-3-carboximidamide (example I, step 5) are dissolved together with 1.04 g (8.91 mmol) of methyl 3-oxobutanoate in 10 ml of absolute toluene under argon and stirred under reflux for 8 hours. A further 8.91 mmol of methyl 3-oxobutanoate are added, and stirring under reflux temperature is continued for 24 hours. This is followed by cooling to 0° C., removal of the precipitated solid by filtration and drying under high vacuum. 1.98 g (72% of theory) of the product are obtained.

LC/MS (method D): $R_t$=3.65 min.
MS (ESIpos): m/z=336 (M+H)+
$^1$H-NMR (200 MHz, CDCl$_3$): δ=2.40 (s, 3H), 5.83 (s, 2H), 6.26 (s, 1H), 7.01-7.16 (m, 2H), 7.20-7.40 (m, 3H), 8.66 (d, 1H), 8.74 (d, 1H), 10.16 (br s, 1H).

Step 7

3-(4-Chloro-6-methyl-2-pyrimidinyl)-1-(2-fluorobenzyl)-1H-pyrazolo[3,4-b]pyridine

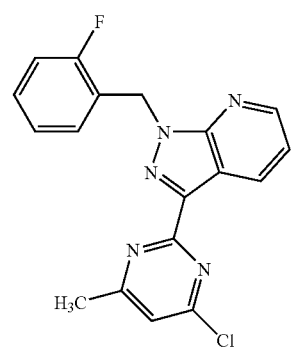

300 mg (0.90 mmol) of 2-[1-(2-fluorobenzyl)-1H-pyrazolo[3,4-b]pyridin-3-yl]-6-methyl-4-pyrimidinol (example I, step 6) are suspended in 2 ml of phosphoryl chloride and stirred at 100° C. After the reaction is complete, a concentrated aqueous sodium carbonate solution is added, and the mixture is extracted with diethyl ether. The organic phase is dried over magnesium sulfate and filtered, and the solvent is removed in vacuo. 256 mg (77% of theory) of the product are obtained.

LC/MS (method D): $R_t$=4.65 min.
MS (ESIpos): m/z=354 (M+H)+
$^1$H-NMR (400 MHz, CDCl$_3$): δ=2.66 (s, 3H), 5.99 (s, 2H), 6.93-7.01 (m, 2H), 7.06 (t, 1H), 7.18 (s, 1H), 7.19-7.26 (m, 1H), 7.31 (dd, 1H), 8.62 (dd, 1H), 8.95 (d, 1H).

EXAMPLE II

Step 1

5-Fluoro-2-[1-(2-fluorobenzyl)-1H-pyrazolo[3,4-b]pyridin-3-yl]-6-methyl-4-pyrimidinol

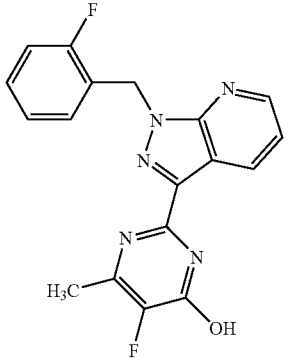

The compound is prepared in analogy to example I, step 6. Starting from 650 mg (2.41 mmol) of 1-(2-fluorobenzyl)-1H-pyrazolo[3,4-b]pyridine-3-carboximidamide (example I, step 5) and ethyl 2-fluoro-3-oxobutanoate, 520 mg (60% of theory) of the product are obtained.

LC/MS (method A): $R_f$=2.51 min.
MS (ESIpos): m/z=354 (M+H)$^+$
$^1$H-NMR (200 MHz, CDCl$_3$): δ=2.43 (d, 3H), 5.83 (s, 2H), 7.00-7.13 (m, 2H), 7.20-7.40 (m, 3H), 8.68 (d, 1H), 8.76 (d, 1H), 10.27 (br s, 1H).

Step 2

3-(4-Chloro-5-fluoro-6-methyl-2-pyrimidinyl)-1-(2-fluorobenzyl)-1H-pyrazolo-[3,4-b]pyridine

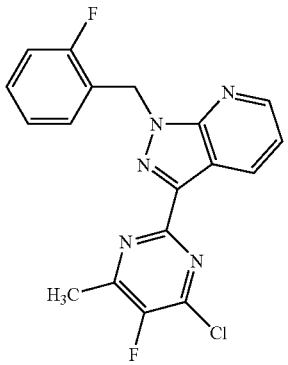

The compound is prepared in analogy to example I, step 7. Starting from 4.70 g (13.30 mmol) of 5-fluoro-2-[1-(2-fluorobenzyl)-1H-pyrazolo[3,4-b]pyridin-3-yl]-6-methyl-4-pyrimidinol (example II, step 1), chromatography of the crude product on silica gel (eluent: DCM/methanol 100:1) results in 4.10 g (83% of theory) of the product.

LC/MS (method A): $R_f$=2.97 min.
MS (ESIpos): m/z=372 (M+H)+
$^1$H-NMR (400 MHz, CDCl$_3$): δ=2.70 (d, 3H), 5.98 (s, 2H), 6.95-7.12 (m, 3H), 7.19-7.23 (m, 1H), 7.32 (dd, 1H), 8.62 (d, 1H), 8.89 (d, 1H).

Exemplary Embodiments

EXAMPLE 1

N-[3-(Ethyloxy)propyl]-2-{1-[(2-fluorophenyl)methyl]-1H-pyrazolo[3,4-b]pyridin-3-yl}-6-methyl-4-pyrimidineamine

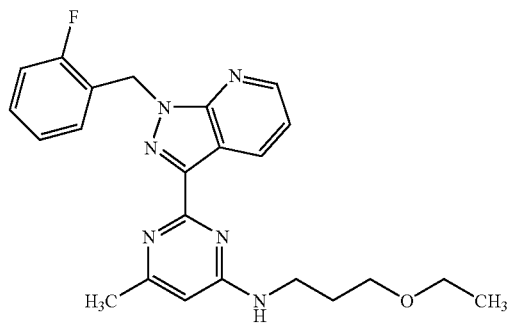

35 mg (0.10 mmol) of 3-(4-chloro-6-methyl-2-pyrimidinyl)-1-(2-fluorobenzyl)-1H-pyrazolo[3,4-b]pyridine (example I, step 7) and 52 mg (0.50 mmol) of 3-(ethyloxy)-propylamine are dissolved in 0.40 ml of DMSO and heated at 60° C. for 48 hours. The reaction mixture is diluted with 0.20 ml of DMSO and then purified by preparative HPLC. 41 mg (98% of theory) of the product are obtained.

LC/MS (method C): $R_f$=2.97 min.
MS (ESIpos): m/z=421 (M+H)$^+$.

The examples listed in the following table can be prepared from the appropriate starting compounds in analogy to the method of example 1:

| Ex. No. | Structure | Analytical data |
|---|---|---|
| 2 | 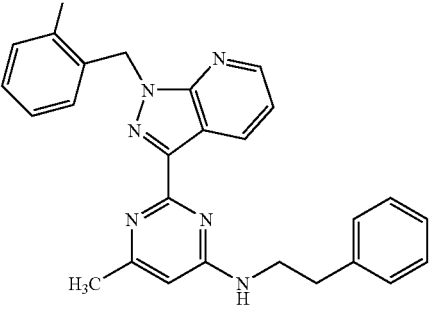 | LC/MS (method C): $R_t$ = 3.23 min.<br>MS (ESIpos): m/z = 439 (M + H)$^+$. |

-continued

| Ex. No. | Structure | Analytical data |
|---|---|---|
| 3 | 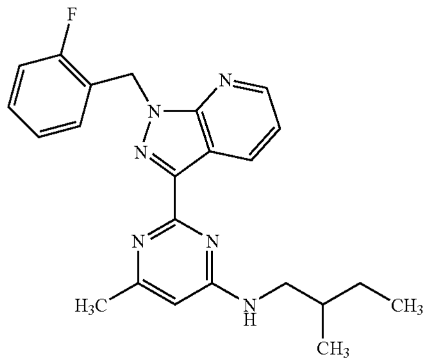 | LC/MS (method C): R_t = 3.24 min. MS (ESIpos): m/z = 405 (M + H)+. |
| 4 | 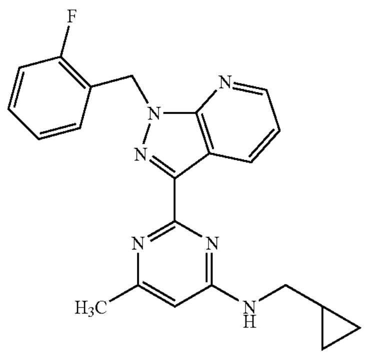 | LC/MS (method C): R_t = 3.02 min. MS (ESIpos): m/z = 389 (M + H)+. |
| 5 | 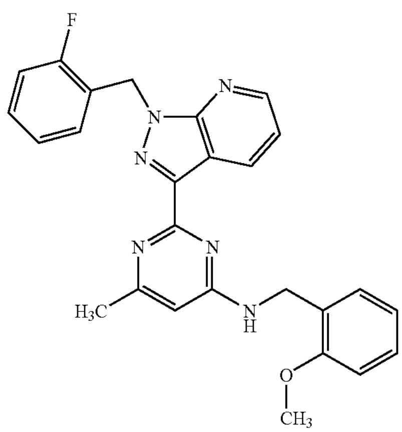 | LC/MS (method C): R_t = 3.21 min. MS (ESIpos): m/z = 455 (M + H)+. |
| 6 | 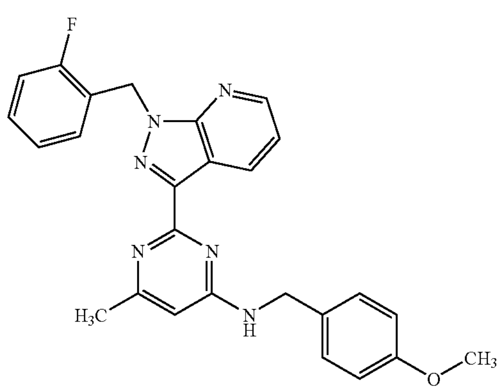 | LC/MS (method C): R_t = 3.15 min. MS (ESIpos): m/z = 455 (M + H)+. |

-continued
| Ex. No. | Structure | Analytical data |
|---|---|---|
| 7 | 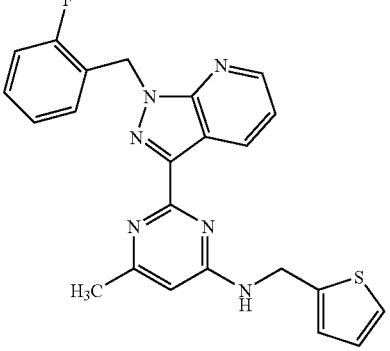 | LC/MS (method C): $R_t$ = 3.12 min.<br>MS (ESIpos): m/z = 431 (M + H)$^+$. |
| 8 | 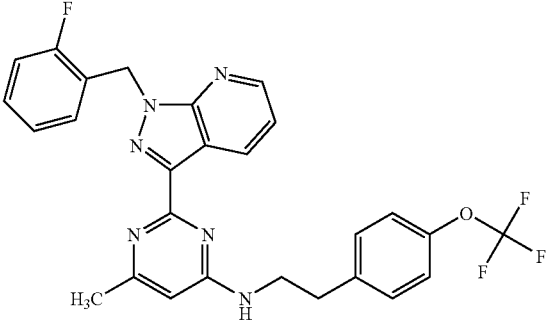 | LC/MS (method C): $R_t$ = 3.47 min.<br>MS (ESIpos): m/z = 523 (M + H)$^+$. |
| 9 | 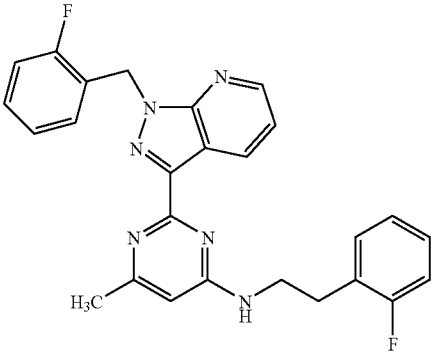 | LC/MS (method C): $R_t$ = 3.24 min.<br>MS (ESIpos): m/z = 457 (M + H)$^+$. |
| 10 | 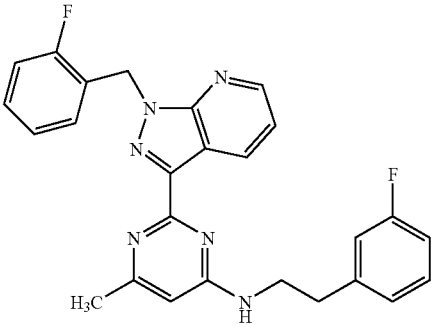 | LC/MS (method C): $R_t$ = 3.25 min.<br>MS (ESIpos): m/z = 457 (M + H)$^+$. |

-continued

| Ex. No. | Structure | Analytical data |
|---|---|---|
| 11 | 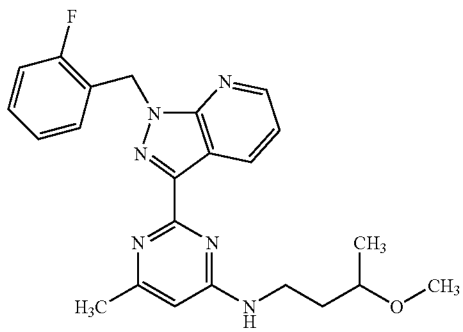 | LC/MS (method C): $R_t$ = 2.95 min.<br>MS (ESIpos): m/z = 421 (M + H)$^+$. |
| 12 | 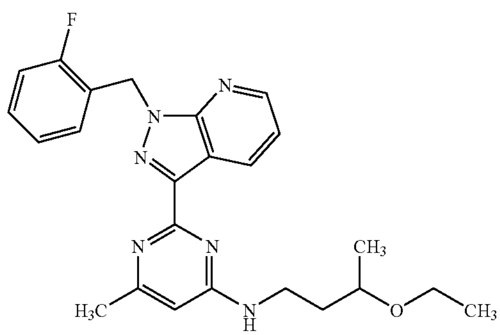 | LC/MS (method C): $R_t$ = 3.07 min.<br>MS (ESIpos): m/z = 435 (M + H)$^+$. |
| 13 | 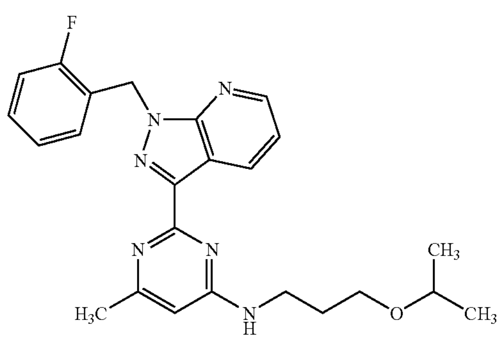 | LC/MS (method C): $R_t$ = 3.09 min.<br>MS (ESIpos): m/z = 435 (M + H)$^+$. |
| 14 | 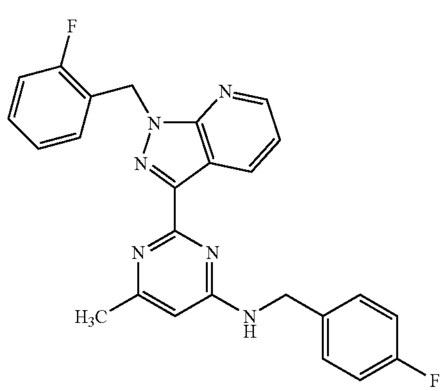 | LC/MS (method C): $R_t$ = 3.20 min.<br>MS (ESIpos): m/z = 443 (M + H)$^+$. |

-continued

| Ex. No. | Structure | Analytical data |
|---|---|---|
| 15 | 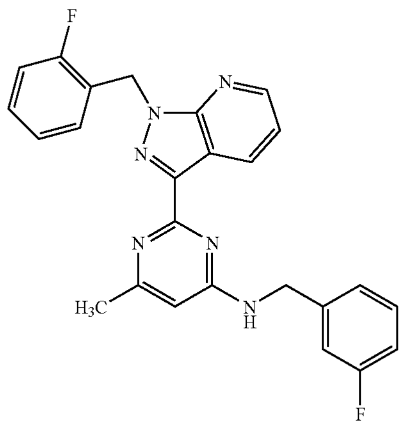 | LC/MS (method C): R$_t$ = 3.20 min.<br>MS (ESIpos): m/z = 443 (M + H)$^+$. |
| 16 | 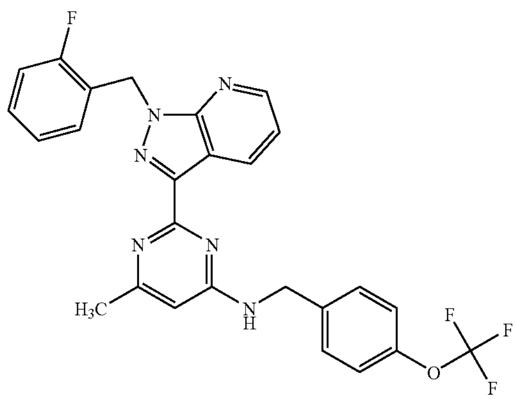 | LC/MS (method C): R$_t$ = 3.49 min.<br>MS (ESIpos): m/z = 509 (M + H)$^+$. |
| 17 | 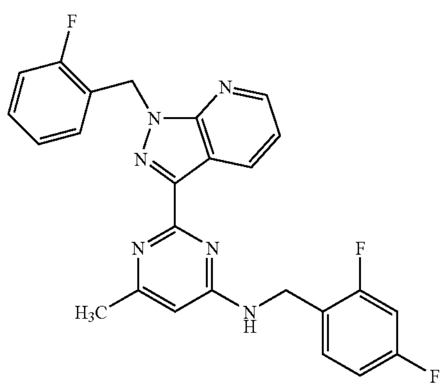 | LC/MS (method C): R$_t$ = 3.27 min.<br>MS (ESIpos): m/z = 461 (M + H)$^+$. |
| 18 | 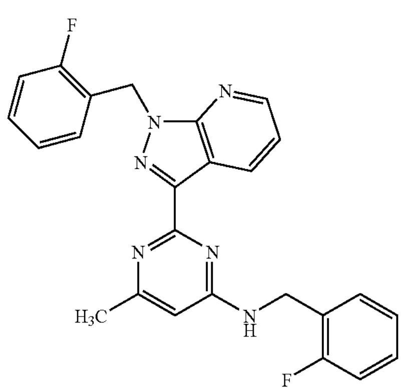 | LC/MS (method C): R$_t$ = 3.20 min.<br>MS (ESIpos): m/z = 443 (M + H)$^+$. |

| Ex. No. | Structure | Analytical data |
|---|---|---|
| 19 | 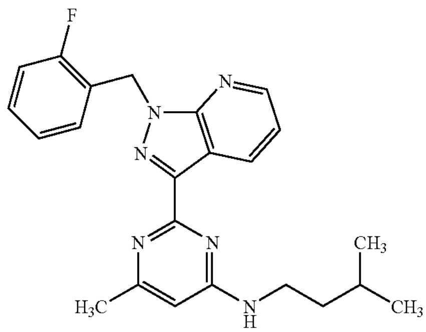 | LC/MS (method C): R$_t$ = 3.25 min.<br>MS (ESIpos): m/z = 405 (M + H)$^+$. |
| 20 | 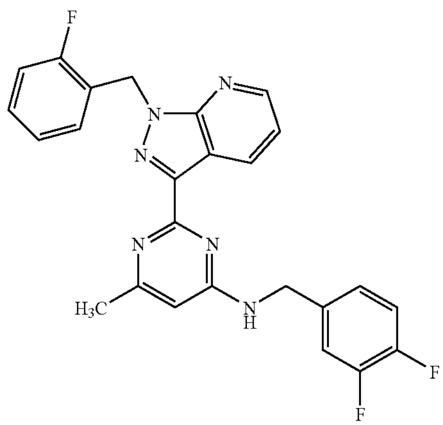 | LC/MS (method C): R$_t$ = 3.27 min.<br>MS (ESIpos): m/z = 461 (M + H)$^+$. |
| 21 | 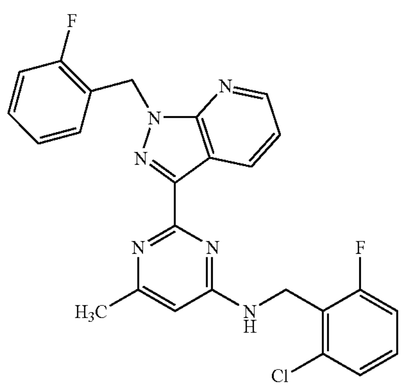 | LC/MS (method C): R$_t$ = 3.32 min.<br>MS (ESIpos): m/z = 477 (M + H)$^+$. |
| 22 | 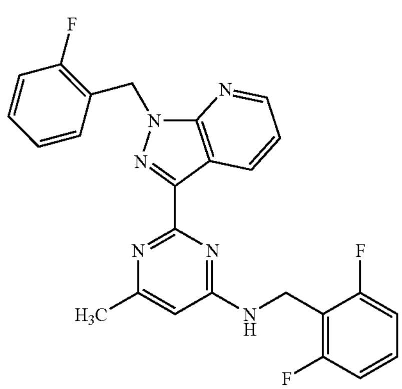 | LC/MS (method C): R$_t$ = 3.21 min.<br>MS (ESIpos): m/z = 461 (M + H)$^+$. |

-continued

| Ex. No. | Structure | Analytical data |
|---|---|---|
| 23 | 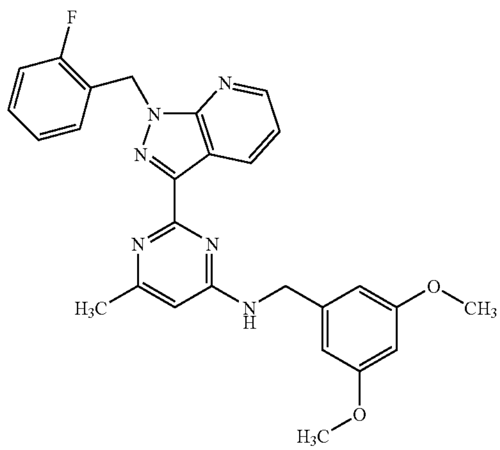 | LC/MS (method C): $R_t$ = 3.18 min.<br>MS (ESIpos): m/z = 484 (M + H)$^+$. |
| 24 | 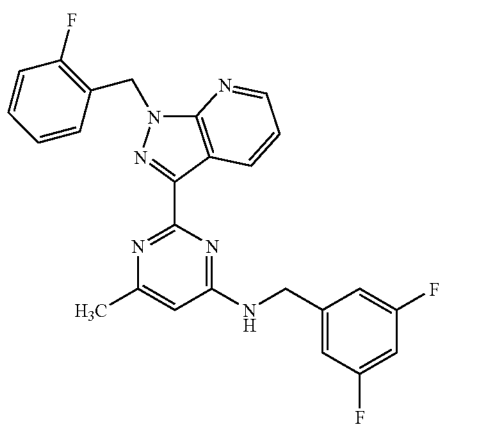 | LC/MS (method C): $R_t$ = 3.29 min.<br>MS (ESIpos): m/z = 461 (M + H)$^+$. |
| 25 | 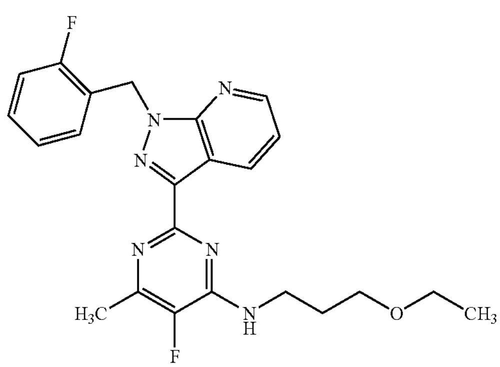 | LC/MS (method C): $R_t$ = 4.07 min.<br>MS (ESIpos): m/z = 439 (M + H)$^+$. |
| 26 | 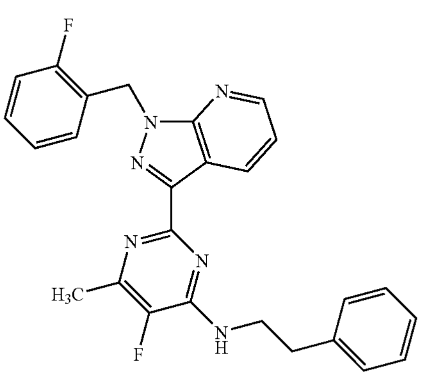 | LC/MS (method C): $R_t$ = 4.60 min.<br>MS (ESIpos): m/z = 457 (M + H)$^+$. |

| Ex. No. | Structure | Analytical data |
|---|---|---|
| 27 | 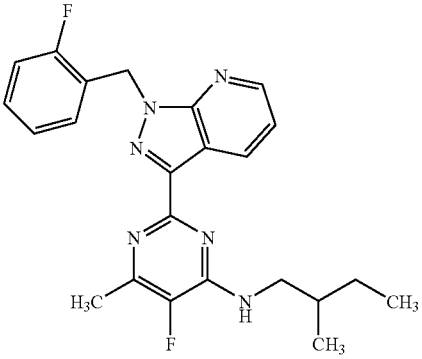 | LC/MS (method C): $R_t$ = 4.61 min.<br>MS (ESIpos): m/z = 423 (M + H)$^+$. |
| 28 | 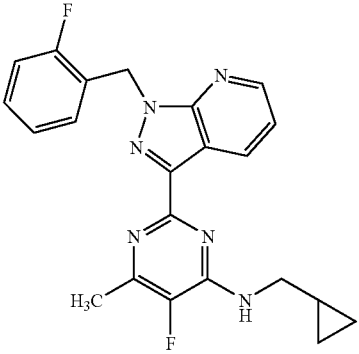 | LC/MS (method C): $R_t$ = 4.16 min.<br>MS (ESIpos): m/z = 407 (M + H)$^+$. |
| 29 | 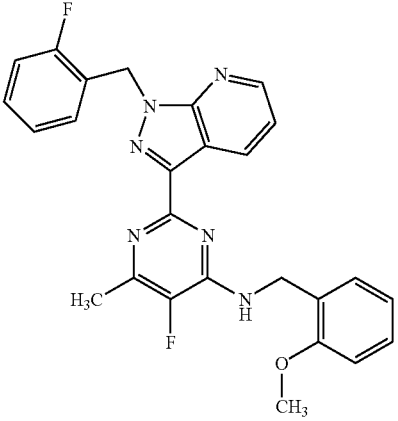 | LC/MS (method C): $R_t$ = 4.51 min.<br>MS (ESIpos): m/z = 473 (M + H)$^+$. |
| 30 | 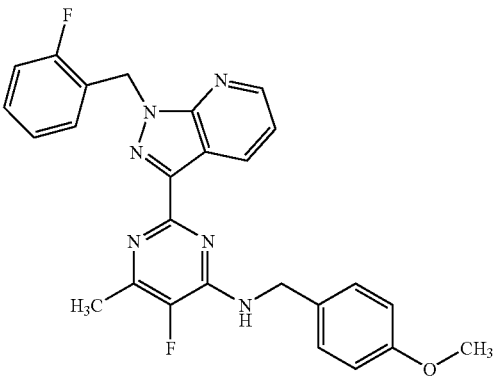 | LC/MS (method C): $R_t$ = 4.40 min.<br>MS (ESIpos): m/z = 473 (M + H)$^+$. |

| Ex. No. | Structure | Analytical data |
|---|---|---|
| 31 | 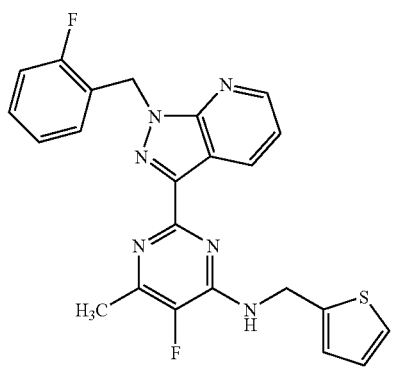 | LC/MS (method C): $R_t$ = 4.45 min.<br>MS (ESIpos): m/z = 449 (M + H)$^+$. |
| 32 | 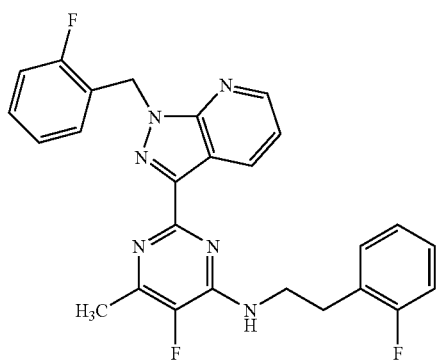 | LC/MS (method C): $R_t$ = 4.61 min.<br>MS (ESIpos): m/z = 475 (M + H)$^+$. |
| 33 | 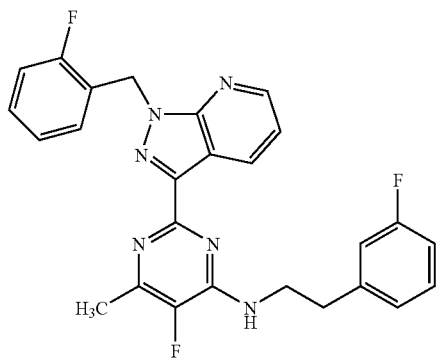 | LC/MS (method C): $R_t$ = 4.65 min.<br>MS (ESIpos): m/z = 475 (M + H)$^+$. |
| 34 | 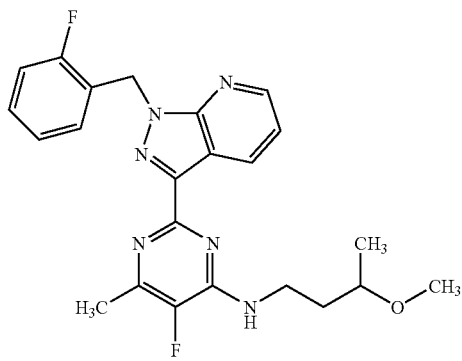 | LC/MS (method C): $R_t$ = 4.00 min.<br>MS (ESIpos): m/z = 439 (M + H)$^+$. |

| Ex. No. | Structure | Analytical data |
| --- | --- | --- |
| 35 | 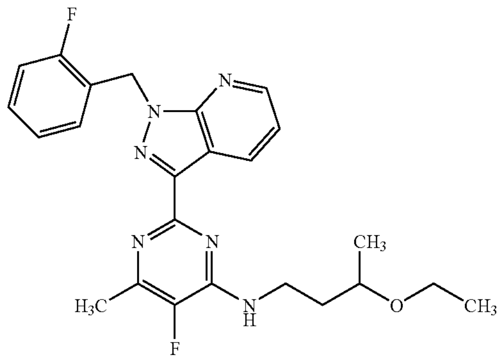 | LC/MS (method C): $R_t$ = 4.29 min.<br>MS (ESIpos): m/z = 453 (M + H)$^+$. |
| 36 | 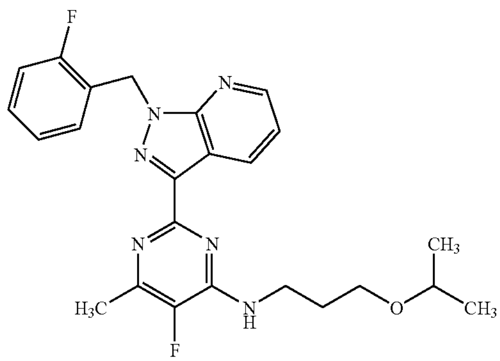 | LC/MS (method C): $R_t$ = 4.35 min.<br>MS (ESIpos): m/z = 453 (M + H)$^+$. |
| 37 | 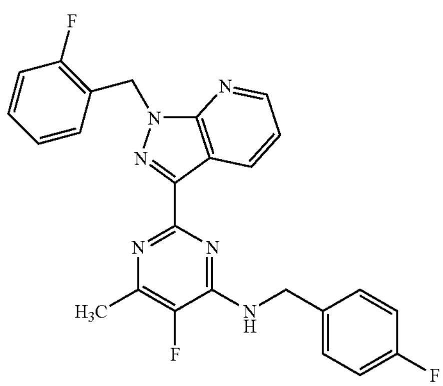 | LC/MS (method C): $R_t$ = 4.56 min.<br>MS (ESIpos): m/z = 461 (M + H)$^+$. |
| 38 | 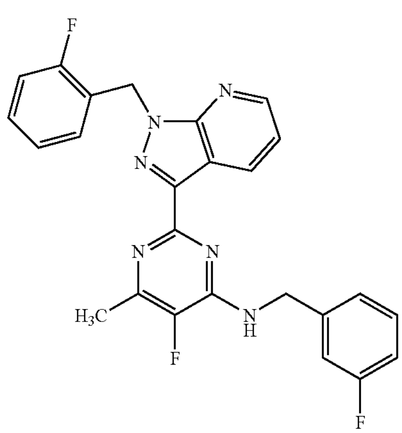 | LC/MS (method C): $R_t$ = 4.57 min.<br>MS (ESIpos): m/z = 461 (M + H)$^+$. |

-continued

| Ex. No. | Structure | Analytical data |
|---|---|---|
| 39 | 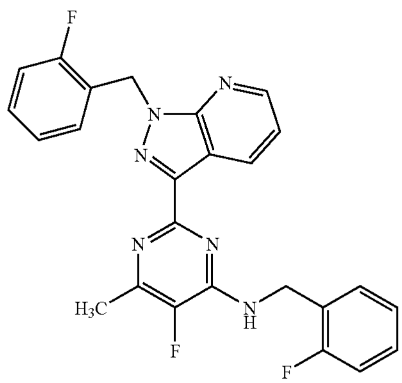 | LC/MS (method C): $R_t$ = 4.61 min. MS (ESIpos): m/z = 461 (M + H)$^+$. |
| 40 | 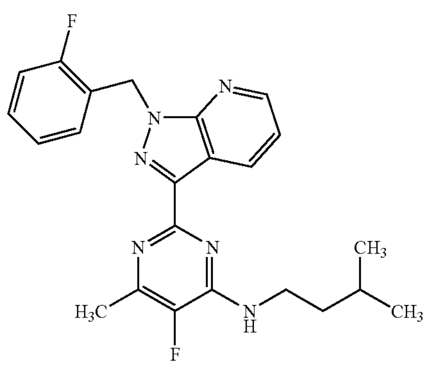 | LC/MS (method C): $R_t$ = 4.62 min. MS (ESIpos): m/z = 423 (M + H)$^+$. |
| 41 | 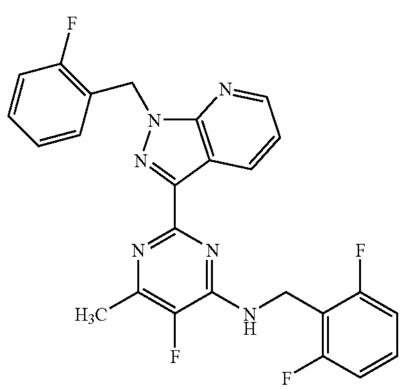 | LC/MS (method C): $R_t$ = 4.60 min. MS (ESIpos): m/z = 479 (M + H)$^+$. |
| 42 | 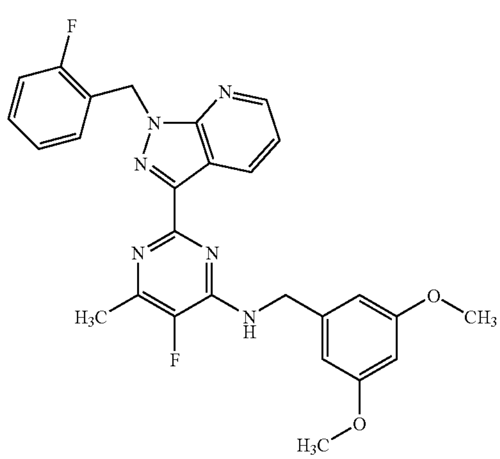 | LC/MS (method C): $R_t$ = 4.41 min. MS (ESIpos): m/z = 503 (M + H)$^+$. |

-continued

| Ex. No. | Structure | Analytical data |
|---|---|---|
| 43 | 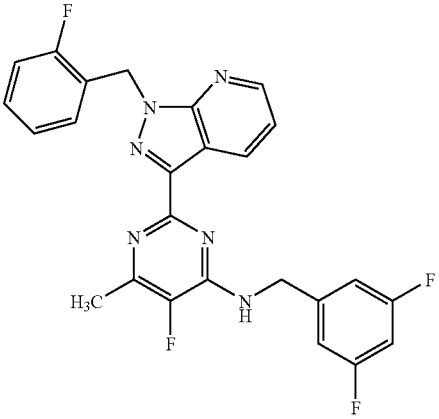 | LC/MS (method C): $R_t$ = 4.68 min.<br>MS (ESIpos): m/z = 479 (M + H)$^+$. |

The invention claimed is:

1. A compound of the formula

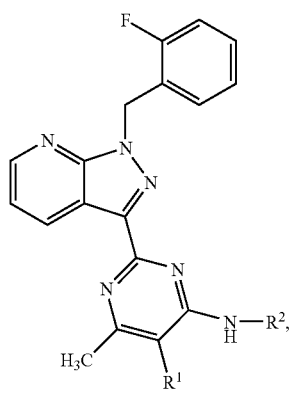

(I)

in which
- $R^1$ is hydrogen or fluorine,
- $R^2$ is $C_1$-$C_6$-alkyl which may be substituted by $C_1$-$C_4$-alkoxy, $C_3$-$C_6$-cycloalkyl, $C_6$-$C_{10}$-aryl, 5- to 6-membered heteroaryl, where $C_6$-$C_{10}$-aryl and 5- to 6-membered heteroaryl may optionally be substituted by up to 3 radicals selected from the group of halogen, $C_1$-$C_4$-alkyl, $C_1$-$C_4$-alkoxyl, trifluoromethoxy, or a salt thereof.

2. The compound as claimed in claim 1, in which
- $R^1$ is hydrogen or fluorine,
- $R^2$ is $C_1$-$C_5$-alkyl which may be substituted by methoxy, ethoxy, isopropoxy, cyclopropyl,
  or
  benzyl, phenethyl, which are optionally substituted by up to 3 radicals selected from the group of fluorine, methyl, methoxy, trifluoromethoxy,
  or
  thienyl,
  or a salt thereof.

3. A process for preparing compounds of the formula (I), characterized in that compounds of the formula

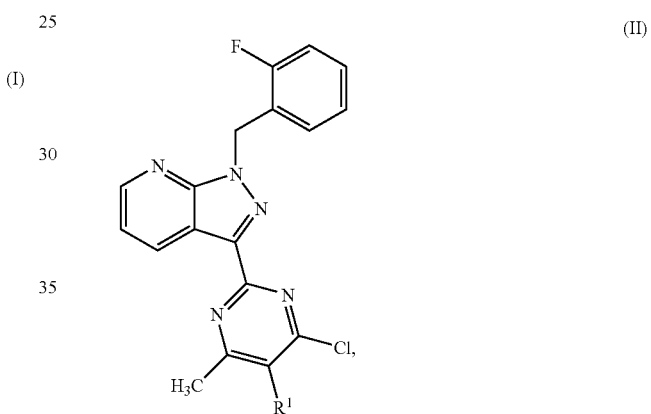

(II)

in which $R^1$ has the meaning indicated in claim 1, are reacted with a compound of the formula $$H_2N-R^2 \quad (III),$$

in which $R^2$ has the meaning indicated in claim 1, and the resulting compounds (I) are reacted where appropriate with the appropriate (i) solvents and/or (ii) bases or acids to give the salts thereof.

4. A medicament comprising at least one of the compounds as claimed in claim 1 mixed together with at least one pharmaceutically acceptable, essentially nontoxic carrier or excipient.

5. A method for the treatment of disorders of learning and/or memory comprising administering to a human or animal an effective amount of compound of claim 1.

6. A method for the treatment of disorders of learning and/or memory comprising administering to a human or animal an effective amount of a medicament of claim 4.

7. A method for controlling disorders of learning and/or memory in humans or animals comprising administering to a human or animal an effective amount of a compound of claim 1.

* * * * *